(12) United States Patent
Nakakado (10) Patent No.: US 8,211,256 B2
(45) Date of Patent: Jul. 3, 2012

(54) METHOD FOR PRODUCING DISPOSABLE WORN ARTICLE

(75) Inventor: Masaki Nakakado, Osaka (JP)

(73) Assignee: Zuiko Corporation, Osaka (JP)

( * ) Notice: Subject to any disclaimer, the term of this patent is extended or adjusted under 35 U.S.C. 154(b) by 434 days.

(21) Appl. No.: 12/526,835

(22) PCT Filed: Mar. 31, 2008

(86) PCT No.: PCT/JP2008/056289

§ 371 (c)(1),
(2), (4) Date: Aug. 12, 2009

(87) PCT Pub. No.: WO2008/126708

PCT Pub. Date: Oct. 23, 2008

(65) Prior Publication Data

US 2010/0051170 A1 Mar. 4, 2010

(30) Foreign Application Priority Data

Apr. 10, 2007 (JP) ................................. 2007-102381

(51) Int. Cl.
*B32B 37/00* (2006.01)

(52) U.S. Cl. ....... 156/73.1; 156/163; 156/229; 156/269; 156/308.4

(58) Field of Classification Search ................. 156/73.1, 156/160, 161, 163, 164, 229, 308.2, 308.4, 156/250, 269
See application file for complete search history.

(56) References Cited

U.S. PATENT DOCUMENTS

| | | |
|---|---|---|
| 4,770,656 A | 9/1988 | Proxmire et al. |
| 5,685,874 A | 11/1997 | Buell et al. |
| 6,994,761 B2 | 2/2006 | Klemp et al. |

FOREIGN PATENT DOCUMENTS

| | | |
|---|---|---|
| JP | 63-243308 | 10/1988 |
| JP | 03-176053 | 7/1991 |
| JP | 04-161152 | 6/1992 |
| JP | 2001-129016 | 5/2001 |
| JP | 2002-369842 | 12/2002 |
| JP | 2006-212307 | 8/2006 |

OTHER PUBLICATIONS

International Search Report for corresponding Application No. PCT/JP2008/056289 dated Jul. 1, 2008.

*Primary Examiner* — James Sells (74) *Attorney, Agent, or Firm* — Renner, Otto, Boisselle & Sklar, LLP (57) ABSTRACT

A method for producing a disposable worn article and a laminated stretchable sheet of the present invention includes: a step of forming stretched elastic sheet pieces F1 from a continuous elastic sheet; a step of carrying continuous webs Wa and Wb to be torso portions; a step of placing the elastic sheet pieces F1 intermittently on the continuous webs Wa and Wb; a step of bonding opposite end portions of the elastic sheet pieces F1 in the longitudinal direction to the continuous webs Wa and Wb by an adhesive, during the placement; an ultrasonic attachment step of forming a laminated stretchable sheet in an overlap portion between an intermediate portion between the opposite end portions of the elastic sheet piece F1 and the continuous webs; a placement step of placing core portions C, each of which forms a crotch portion 33, between adjacent ones of the elastic sheet pieces F1; and a step of cutting off the laminated stretchable sheet between adjacent ones of the core portions C.

10 Claims, 6 Drawing Sheets

METHOD FOR PRODUCING DISPOSABLE WORN ARTICLE

TECHNICAL FIELD

The present invention relates to a method for producing a disposable worn article using a laminated stretchable sheet.

BACKGROUND ART

In the prior art, there are cases where a laminated stretchable sheet including two non-woven fabrics and a thermoplastic elastic sheet placed therebetween is used as a composite sheet for use in a disposable diaper, or the like, particularly, as a composite sheet for use in a waist portion of a pants-type diaper, or the like, in order to improve the fit of the diaper (see the first and second patent documents).

[First Patent Document] Japanese Laid-Open Patent Publication No. 2001-129016 (Abstract)

[Second Patent Document] U.S. Pat. No. 6,994,761 B2

DISCLOSURE OF THE INVENTION

Japanese Laid-Open Patent Publication No. 2001-129016 describes a method for producing a disposable worn article by intermittently bonding elastic sheet pieces on front and rear girth webs, and placing absorbent body webs between adjacent elastic sheet pieces.

However, when elastic sheet pieces are bonded by an adhesive on girth webs, it is not possible to obtain sufficient stretching of the elastic sheet pieces. Moreover, the use of an adhesive for the bonding introduces stiffness to the girth web or deteriorates the feel of the girth web.

On the other hand, the specification of U.S. Pat. No. 6,994,761 describes attaching an elastic sheet piece to a web at a plurality of positions by thermal welding or ultrasonic attachment.

With this method, however, it is difficult to attach the elastic sheet piece to the web while holding the elastic sheet piece in a stretched state.

It is therefore a primary object of the present invention to provide a method for producing a disposable worn article with a sufficient stretchability, a good feel, and a desirable productivity.

A method for producing a disposable worn article of the present invention is a method for producing a disposable worn article including a torso portion covering a torso of a wearer, and a crotch portion covering a crotch of the wearer, the method including: a step of forming stretched elastic sheet pieces from a continuous elastic sheet; a step of carrying a continuous web to be the torso portion in a longitudinal direction of the continuous web; a step of placing the elastic sheet pieces intermittently on the continuous web, with a stretch direction of the stretched elastic sheet pieces being aligned with the longitudinal direction; a step of bonding opposite end portions of each of the elastic sheet pieces in the longitudinal direction to the continuous web by an adhesive, during the placing step; an ultrasonic attachment step of applying a vibration energy on an overlap portion in which an intermediate portion of one of the elastic sheet pieces between the opposite end portions and the continuous web overlap with each other, thereby welding the intermediate portion to the continuous web, and forming a laminated stretchable sheet; a placement step of placing a core portion to be the crotch portion between adjacent ones of the elastic sheet pieces on the laminated stretchable sheet; and a step of cutting off the laminated stretchable sheet between adjacent ones of the core portions.

According to the present invention, the elastic sheet and the continuous web are welded to each other by applying a vibration energy on an overlap portion therebetween, and it is therefore not necessary to use an adhesive. As a result, it is possible to achieve a good feel and a sufficient stretchability.

Since the attachment is done by applying a vibration energy on the intermediate portion between the opposite end portions of the elastic sheet piece in the longitudinal direction, i.e., the flow direction, after the opposite end portions are bonded to the continuous web, the elastic sheet piece can be ultrasonically attached to the web while holding the elastic sheet piece in a stretched state. Therefore, since it is not necessary to separately provide an apparatus, etc., for holding the elastic sheet piece in a stretched state, the process is easy, and the productivity will not be lowered.

In the present invention, it is preferred that the method further includes: a step of stretching the elastic sheet in a longitudinal direction; a step of carrying a non-woven fabric, which forms a portion of the torso portion and which is to be an inner sheet to be in contact with a skin surface of the wearer; a step of laying the elastic sheet in a stretched state on the non-woven fabric; a step of bonding by an adhesive a portion of an overlap portion between the non-woven fabric and the elastic sheet laid on each other; and a step of cutting off the non-woven fabric and the elastic sheet, which have been bonded together, to thereby obtain a cut-off panel including one of the elastic sheet pieces therein, wherein the step of forming the elastic sheet piece is performed by these steps.

In the present invention, it is preferred that bonding portions in which the non-woven fabric and the elastic sheet are bonded together are formed in the opposite end portions of the elastic sheet piece in the stretch direction; and the placement step is performed so that the core portion covers at least a portion of the bonding portion.

According to this embodiment, the bonding portions, which have been hardened by an adhesive, are covered by the soft core portion to be in contact with the skin surface of the wearer, and therefore the bonding portions will not be in contact with the skin surface of the wearer. Therefore, it is possible to suppress stiffness and discomfort, and to thus further improve the wearability, etc.

In one embodiment of the present invention, the torso portion includes a front torso portion covering an abdominal portion of the wearer, and a rear torso portion covering a back portion of the wearer; and the elastic sheet piece is placed on each of the torso portions, with the core portion placed so as to bridge between the front torso portion and the rear torso portion.

In such a case, the front and rear torso portions are both stretchable.

In such a case, it is preferred that the front torso portion and the rear torso portion are a pair of continuous webs placed apart from each other, and the method includes a step of carrying the pair of continuous webs in parallel to each other.

According to such an embodiment, it is possible to efficiently produce a pants-type diaper.

In one embodiment, the method may further include, after the placement step, a step of slitting the laminated stretchable sheet into a plurality of pieces along a carrying direction of the laminated stretchable sheet.

It gives a higher productivity to slit a single laminated stretchable sheet into two or more pieces, than to separately produce a pair of laminated stretchable sheet pieces.

In one embodiment of the present invention, the method further includes a step of sandwiching the elastic sheet piece between the continuous web and another web different from the continuous web, wherein the two webs are non-woven fabrics containing thermoplastic fibers therein, and the elastic sheet is a thermoplastic resin sheet, wherein the ultrasonic attachment step is performed by applying a vibration energy, at a plurality of attachment positions, on an overlap portion between the two non-woven fabrics and the elastic sheet piece, thereby welding together the two non-woven fabrics and the elastic sheet piece; and in the ultrasonic attachment step, vent holes are formed in the elastic sheet piece, only in a portion of an outer edge of the attachment positions.

According to this production method, the non-woven fabrics and the elastic sheet pieces are attached together by the application of a vibration energy, without using an adhesive, and thus there will be no stiffness, etc., due to an adhesive. Therefore, it is possible to produce a laminated stretchable sheet that will not deteriorate the wearability or the feel.

In the ultrasonic attachment step, the vibration energy is applied to the attachment positions for welding the two non-woven fabrics with the elastic sheet piece, while ripping a portion of the outer edge of the attachment positions to thereby form vent holes in the elastic sheet. Therefore, there is no need for a separate step for forming vent holes.

Note that the "elastic sheet" may be a film-like elastic sheet, which is an elastic film, for example.

DESCRIPTION OF THE REFERENCE NUMERALS

31: Front torso portion
32: Rear torso portion
33: Crotch portion
A1, A2: Bonding area (bonding portion)
C: Core portion
F: Elastic sheet
F1: Elastic sheet piece
P: Cut-off panel
W1: First non-woven fabric (Non-woven fabric to be inner sheet)
X: Carrying direction (flow direction)

BEST MODE FOR CARRYING OUT THE INVENTION

[Embodiment 1]

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

One embodiment of the present invention will now be described with reference to the drawings.

The following description will be directed to a diaper, as an example of a disposable worn article.

Figure 6:
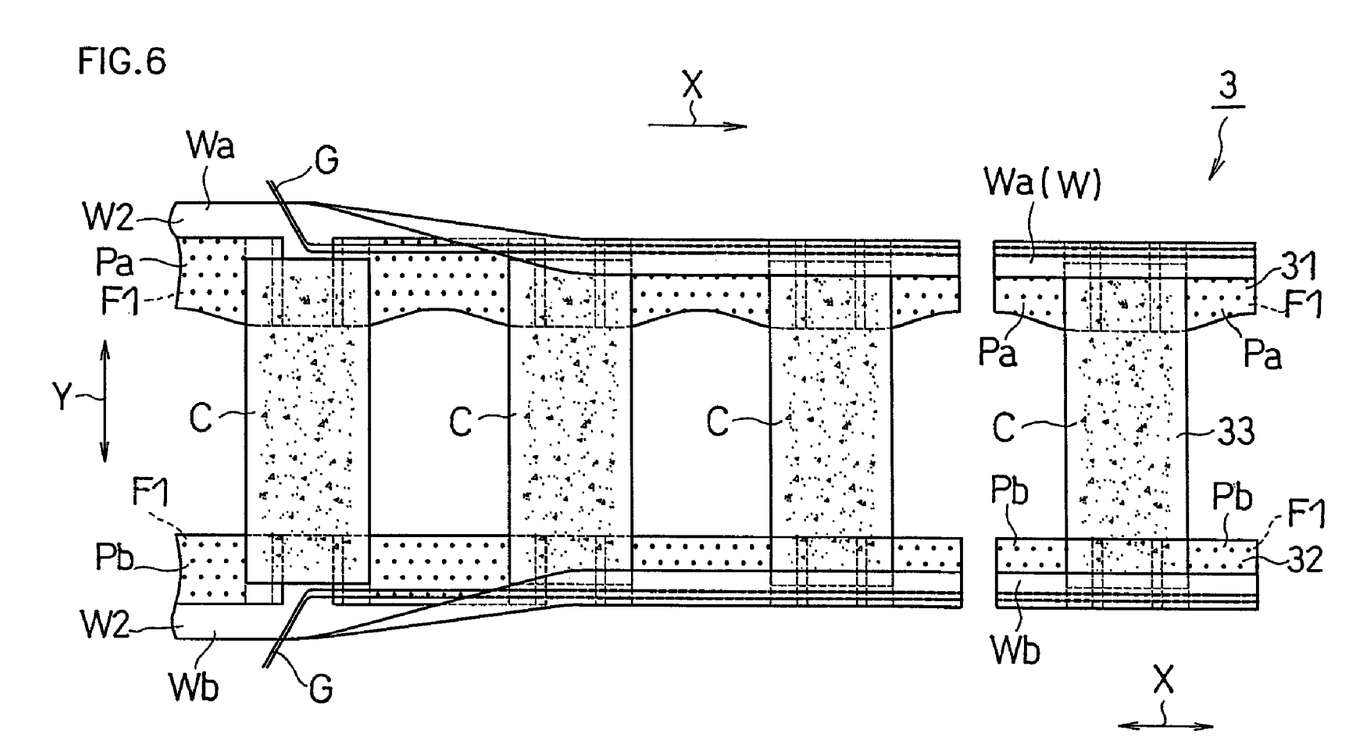
FIG. 6 is a schematic plan view showing a method for producing a worn article.

Diaper 3:

As shown in FIG. 6, a diaper 3 includes torso portions 31 and 32 covering the torso of the wearer, and a crotch portion 33 covering the crotch of the wearer. The crotch portion 33 is formed by a core portion C including an absorbent body.

The torso portions 31 and 32 include the rear torso portion 31 covering a back portion of the wearer, and the front torso portion 32 covering an abdominal portion of the wearer. The core portion C is placed so as to bridge between the rear torso portion 31 and the front torso portion 32.

The rear torso portion 31 and the front torso portion 32 are divided laminated sheets Wa and Wb, respectively, which are obtained by dividing a laminated stretchable sheet W in the width direction Y. The laminated stretchable sheet W will now be described.

Figure 1:
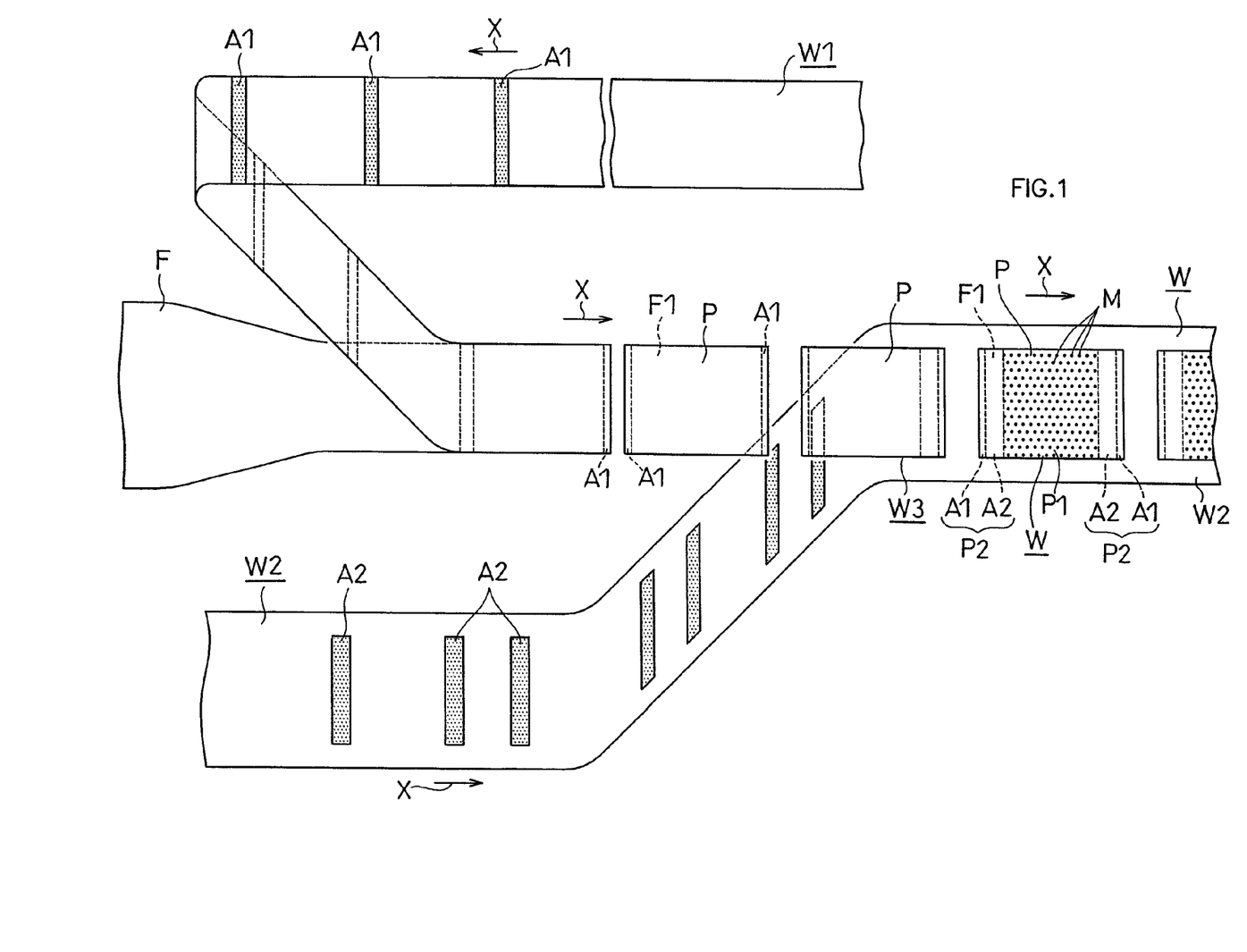
FIG. 1 is a schematic perspective view showing a method for producing a laminated stretchable sheet according to one embodiment of the present invention.

Laminated Stretchable Sheet W:

First, a square cut-off panel P shown in FIG. 1 is produced. The cut-off panel P is obtained by laying an elastic sheet F in a stretched state on a first non-woven fabric W1 to be the inner sheet to be in contact with the skin surface of the wearer, and then cutting the laminate. The cut-off first non-woven fabric W1 and a cut-off elastic sheet piece F1 in the cut-off panel P are bonded to each other by an adhesive in first bonding areas A1 and A1 along opposite end portions of the cut-off panel P in the longitudinal direction X, which are portions of the overlap portion therebetween.

Then, the cut-off panels P are placed at a predetermined interval on a second non-woven fabric W2, which is a continuous web, to thereby form composite sheet W3 portions. Note that the cut-off panel P is placed on the surface to be in contact with the skin surface of the wearer, and is bonded to the second non-woven fabric W2 by an adhesive in second bonding areas A2 and A2 along opposite end portions thereof.

Therefore, in the composite sheet W3 portion, the thermoplastic elastic sheet piece F1 is sandwiched between the two, first and second, non-woven fabrics W1 and W2 containing thermoplastic fibers therein. In the composite sheet W3, opposite end portions P2 of the elastic sheet piece F1 are bonded to the non-woven fabrics W1 and W2 by an adhesive in the first and second bonding areas A1 and A2.

At a plurality of attachment positions M of an intermediate portion P1 of the composite sheet W3, the opposite sides (both surfaces) of the elastic sheet piece F1 are welded respectively to the non-woven fabrics W1 and W2 by ultrasonic attachment to be described below, thereby producing the laminated stretchable sheet W.

Figure 2A:
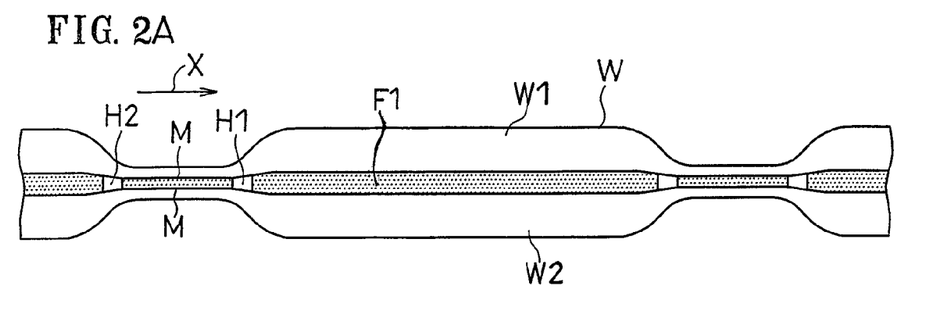
FIG. 2A is a schematic cross-sectional view of a composite stretchable sheet.
Figure 2B:
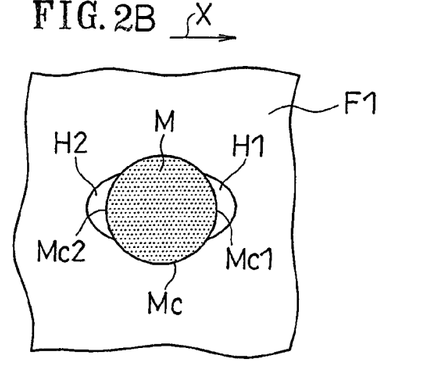
FIG. 2B is an enlarged schematic plan view of an elastic sheet.
Figure 2C:
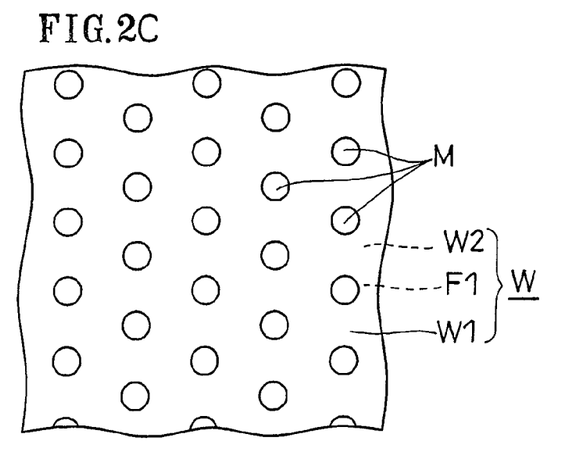
FIG. 2C is a schematic plan view of a composite stretchable sheet.

In the laminated stretchable sheet W, the elastic sheet piece F1 is attached to the first non-woven fabric W1 and the second non-woven fabric W2 at the attachment positions M in the intermediate portion P1 of the composite sheet W3, as shown in FIG. 2C, and vent holes H1 and H2 are formed through the elastic sheet piece F1 in portions Mc1 and Mc2 of an outer edge Mc of the attachment position M, as shown in FIG. 2B.

Sealing Apparatus 1:

Next, an example of a sealing apparatus used for the ultrasonic attachment will be described.

Figure 3:
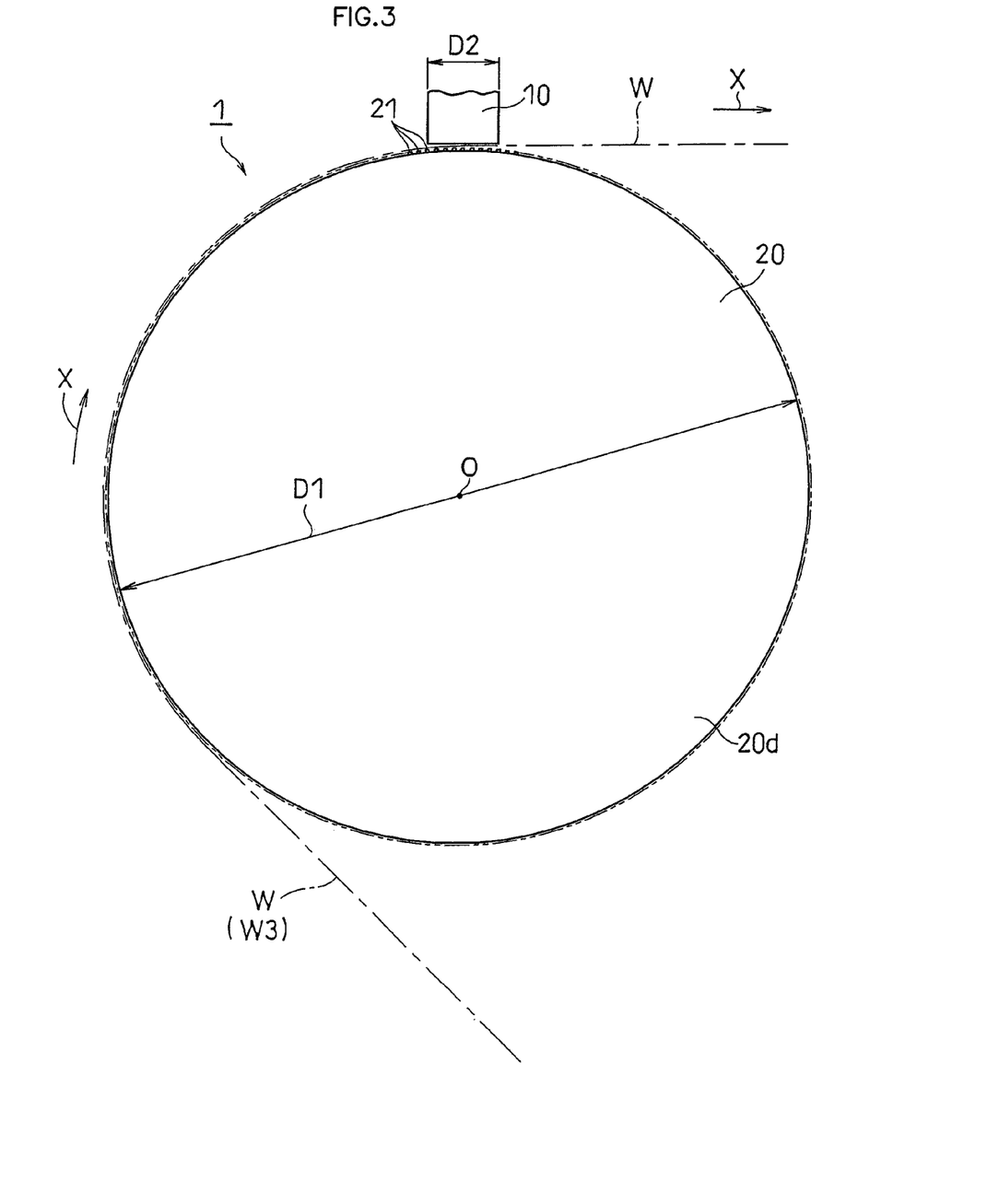
FIG. 3 is a schematic side view showing a sealing apparatus.

As shown in FIG. 3, a sealing apparatus 1 includes an anvil 20 having a large number of protrusions 21 corresponding to the attachment positions M (FIG. 1) for carrying the composite sheet W3, and a horn 10 for applying a vibration energy on the composite sheet W3 in cooperation with the anvil 20. The horn 10 has a flat head surface.

In the anvil 20, the large number of protrusions 21 are formed along the periphery of a drum 20d that rotates about the axis including the point O. The composite sheet W3 is carried in the flow direction X, entailed by the rotation of the drum 20d. The protrusions 21 are provided on the drum 20d at positions corresponding to the pattern of the attachment positions M shown in FIG. 2C.

Figure 4A:
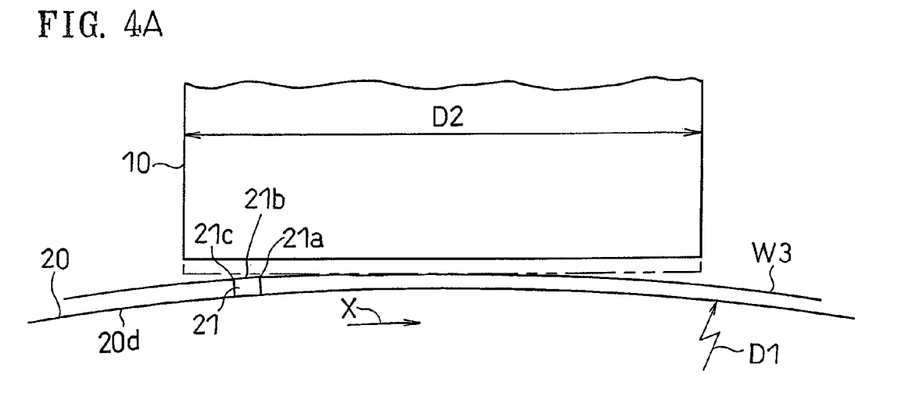
FIGS. 4A, 4B and 4C are enlarged schematic side views showing a method for producing a laminated stretchable sheet.
Figure 4B:
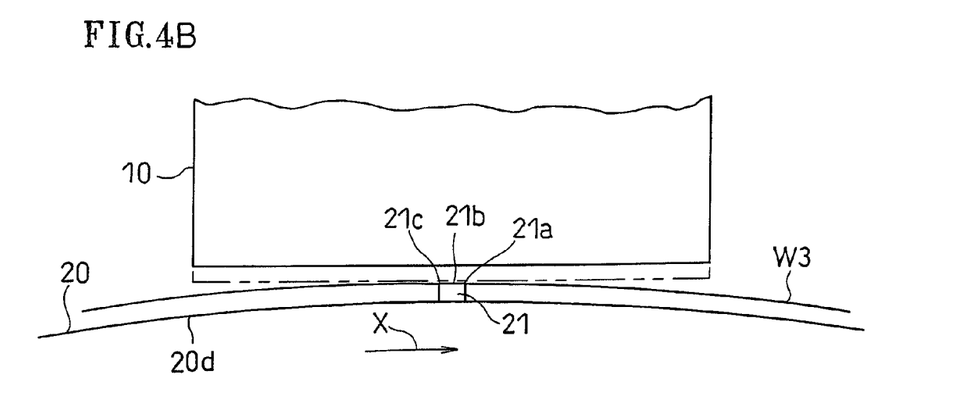
Figure 4C:
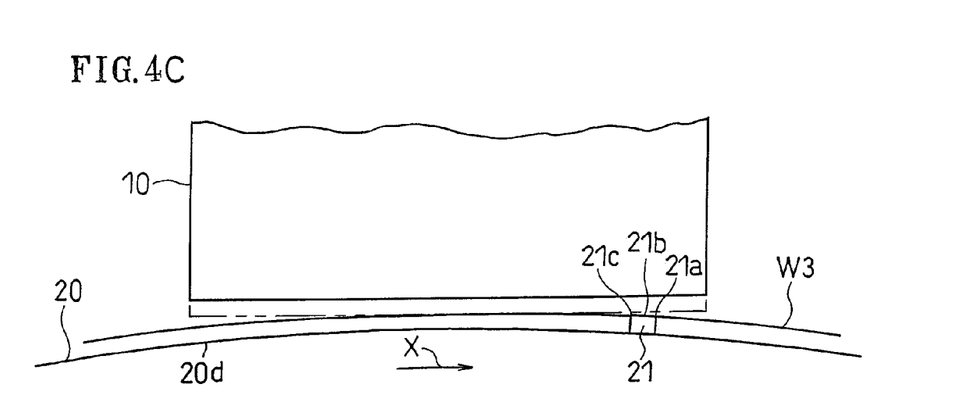

FIGS. 4A, 4B and 4C show only one of the large number of protrusions 21. The protrusion 21 is formed in a generally cylindrical shape. The protrusion 21 includes a flat portion 21b which is flat and capable of facing the horn 10, and edge portions 21a and 21c, which are portions of the peripheral edge of the flat portion 21b of the generally cylindrical shape.

Production Method:

Next, a method for producing a worn article will be described.

First, the elastic sheet F shown in FIG. 1 is stretched in the longitudinal direction (flow direction) X while being carried along.

On the other hand, the first non-woven fabric W1 (an example of a continuous web) is carried along, which forms a portion of the torso portion and which is to be the inner sheet to be in contact with the skin surface of the wearer.

An adhesive is applied in advance on the first bonding areas A1 of the first non-woven fabric W1. As the elastic sheet F in a stretched state is placed while being laid on the first non-woven fabric W1, the elastic sheet F and the first non-woven fabric W1 are bonded to each other by the adhesive in the first bonding area A1 (a portion of the overlap).

The first non-woven fabric W1 and the elastic sheet F, which have been bonded together, are cut off, to thereby obtain the cut-off panel P including the elastic sheet piece F1 therein.

Herein, the first bonding areas A1 are defined at predetermined regular intervals. After the bonding, the first bonding area A1 portion is divided in two equally in the longitudinal direction X, thereby producing the cut-off panel P. Therefore, the cut-off first non-woven fabric W1 and the cut-off elastic sheet piece F1 in the cut-off panel P are bonded to each other in the first bonding areas A1 and A1 along opposite end portions of the cut-off panel P in the longitudinal direction X, which are portions of the overlap portion therebetween.

On the other hand, the second non-woven fabric W2, which is a continuous web to be a portion of the torso portion, is carried in the longitudinal direction X of the second non-woven fabric W2.

The cut-off panels P are placed intermittently on the second non-woven fabric W2 with the stretch direction of the stretched elastic sheet piece F1 being aligned with the longitudinal direction X.

Herein, an adhesive is applied in advance at predetermined regular intervals on the second bonding areas A2 of the second non-woven fabric W2. During the placement, the opposite end portions of the elastic sheet piece F1 in the longitudinal direction X are bonded by the adhesive to the second bonding areas A2 of the second non-woven fabric W2.

As the cut-off panel P is placed on the second non-woven fabric W2, there is produced the composite sheet W3 portion, in which the elastic sheet piece F1 in a stretched state is sandwiched between the two non-woven fabrics W1 and W2. The opposite end portions P2 of the elastic sheet piece F1 are bonded to the first non-woven fabric W1 and the second non-woven fabric W2 in the first bonding areas A1 and A1 and the second bonding areas A2 and A2, respectively, and the intermediate portion P1 between the opposite end portions P2 is not yet at this point bonded to the non-woven fabrics W1 and W2.

Note that while the first bonding areas A1 and the second bonding areas A2 are shown not to overlap with each other for an easier understanding of the illustration, the two bonding areas A1 and A2 may overlap with each other. Since the stretching area is smaller when the two bonding areas A1 and A2 do not overlap with each other, it is preferred that the two bonding areas A1 and A2 overlap with each other. In order to suppress the stiffness felt when worn, due to the bonding portions overlapping with each other, it is preferred that the two bonding areas A1 and A2 do not overlap with each other. The adhesive may be, for example, a hotmelt resin, or the like.

Then, a vibration energy is applied by the sealing apparatus 1 on the overlap portion between the intermediate portion P1 of the elastic sheet piece F1 and the non-woven fabrics W1 and W2, thereby welding the two non-woven fabrics W1 and W2 with the elastic sheet F in a stretched state at the attachment positions M. By the welding, the laminated stretchable sheet W is produced.

On the other hand, during the welding, the vent holes H1 and H2 are formed at the opposite end portions in the longitudinal direction X of the outer edge Mc of the attachment position M in the elastic sheet F, as shown in FIGS. 2A and 2B.

Note that the principle on which the vent holes H1 and H2 are formed will be described later.

Figure 5:
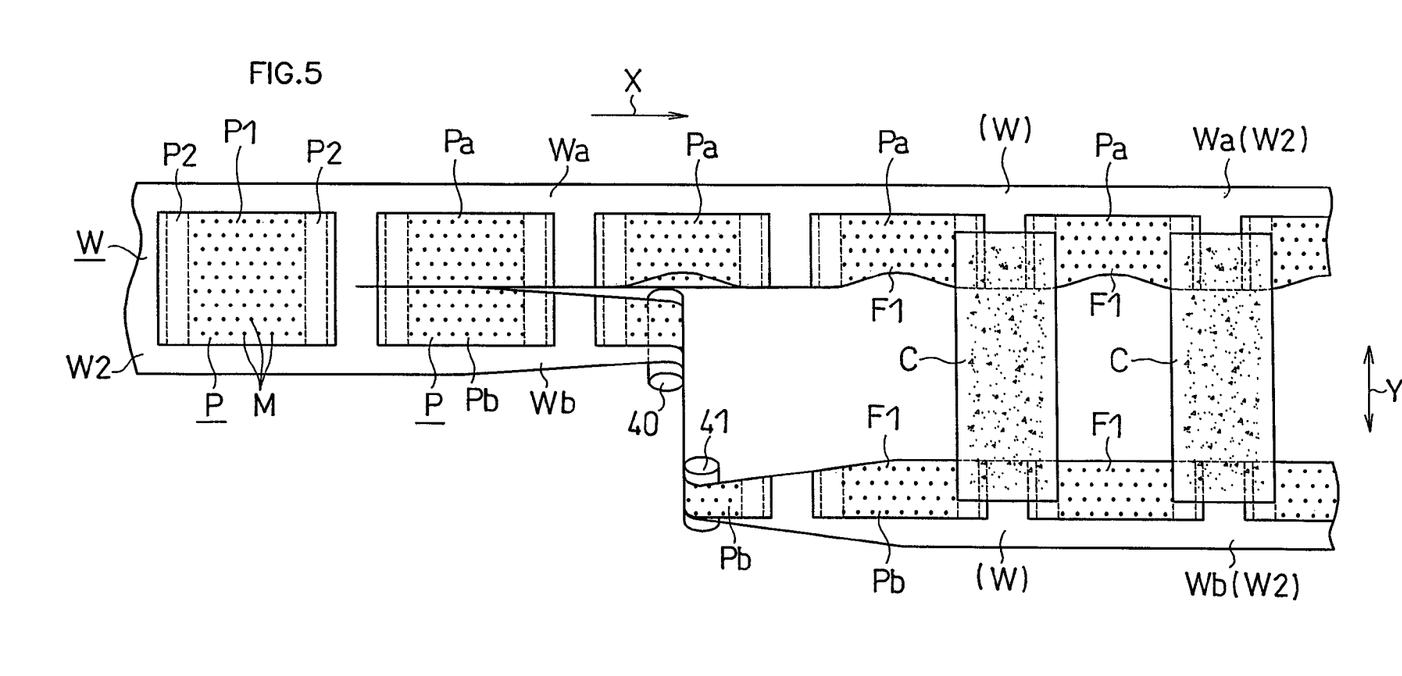
FIG. 5 is a schematic plan view showing a method for producing a worn article.

Then, as shown in FIG. 5, after the step of placement on the second non-woven fabric W2, the cut-off panel P, being in a state of the laminated stretchable sheet W, is slit into two along the carrying direction X of the laminated stretchable sheet W. By the slitting, the laminated stretchable sheet W is divided into the divided laminated sheets Wa and Wb. Thus, a first cut-off panel Pa is attached to the first continuous web Wa, and a second divided cut-off panel Pb is attached to the second continuous web Wb.

After the slitting, by means of a pair of rollers 40 and 41, the second continuous web Wb is moved away from the first continuous web Wa in the width direction Y, and the pair of divided laminated sheets Wa and Wb are carried in parallel to each other. Portions of the divided laminated sheets Wa and Wb may be trimmed so as to conform to the body shape of the wearer.

Then, the core portion C is placed and bonded so as to bridge between the divided laminated sheets Wa and Wb.

The core portions C are placed between adjacent elastic sheet pieces F1 in the laminated stretchable sheet W. That is, the core portions C, forming the crotch portions 33 (FIG. 6), are placed between adjacent elastic sheet pieces F1 in the divided laminated sheets Wa and Wb, obtained by dividing the laminated stretchable sheet W.

As shown in FIG. 5, the core portion C may be placed so that portions thereof overlap with portions of adjacent cut-off panels Pa.

Herein, as described above, the first bonding areas A1 and the second bonding areas A2, in which the first and second non-woven fabrics W1 and W2 and the elastic sheet piece F1 are bonded together, are provided at opposite end portions in the stretch direction X of the elastic sheet piece F1. The core portion C is placed so as to cover the bonding areas A1 and A2. Therefore, portions that have been hardened by the adhesive are covered by the soft core portion C, and will not be in direct contact with the skin surface of the wearer. As a result, stiffness and discomfort are suppressed.

After the core portion C is placed, elastic materials G, which are rubber threads, for example, are bonded to outer portions of the cut-off panels Pa, which are on the outer side of the cut-off panels Pa in the width direction Y, as shown in FIG. 6. Then, outer portions of the divided laminated sheets Wa and Wb, which are on the outer side of the divided laminated sheets Wa and Wb in the width direction Y, are folded back to be bonded together.

Then, the divided laminated sheets Wa and Wb are cut off between adjacent core portions C so as to be separated into individual diapers 3, thus producing the diapers 3.

Principle on which Vent Holes H1 and H2 are Formed:

Next, the principle on which the vent holes H1 and H2 are formed will be described with reference to FIGS. 4A, 4B and 4C. Note that in the following description, the composite sheet W3 is denoted simply by a single solid line, and one of the protrusions 21 is illustrated.

Referring to FIG. 4A, first, as one protrusion 21 starts facing the horn 10, only a portion of the protrusion 21 contacts the horn 10 via the composite sheet W3 because the drum 20d has a curvature. That is, as the frontward portion 21a of the peripheral edge of the edge portion of the protrusion 21 (the end portion on the downstream side in the rotation direction of the drum 20d) contacts the vibrating horn 10, the elastic sheet F shown in FIG. 2A is cut along this contact portion, thus forming a slit in the elastic sheet F in a stretched state. Due to the tensile force of the elastic sheet F, the slit widens in the stretch direction (the longitudinal direction X), thus forming the first vent hole H1.

Then, as shown in FIG. 4B, as the drum 20d rotates, the flat portion 21b of the protrusions 21 contacts the vibrating horn 10, thereby ultrasonically welding the non-woven fabrics W1 and W2 and the elastic sheet F with each other.

After the welding, as shown in FIG. 4C, as the drum 20d further rotates and the rearward portion 21c of the peripheral edge of the edge portion of the protrusions 21 contacts the vibrating horn 10, the elastic sheet F shown in FIG. 2A is cut, as described above, along this contact portion, thus forming the second vent hole H2 in the elastic sheet F.

Thus, as shown in FIG. 2B, in the elastic sheet F, the attachment positions M at which the elastic sheet F is welded to the non-woven fabrics W1 and W2 are formed, and the vent holes H1 and H2 are formed by the cut portions Mc1 and Mc2, obtained by cutting only the frontward and rearward portions, in the flow direction X, of the outer edge Mc of the attachment position M. Herein, since the elastic sheet F is carried in a stretched state, as described above, the elastic sheet F is easily cut when a cutting force is applied on the elastic sheet F by the edge portions 21a and 21c of the protrusion 21. Moreover, since the elastic sheet F is cut in a slit shape by the edge portions 21a and 21c, the vent holes H1 and H2 will be slightly widened in the flow direction X, as shown in FIG. 2B.

Next, a diameter D1 of the drum 20d of FIG. 3 and a width D2 of the horn shown will be discussed.

As described above, in order for the frontward and rearward portions in the rotation direction of the protrusion 21 to serve as edges, the diameter D1 of the drum 20d needs to be small enough, and the width D2 of the horn 10 needs to be large enough.

On the other hand, the diameter D1 of the drum 20d needs to be large enough in view of the mechanical strength.

In view of the above, the diameter D1 of the drum 20d is preferably 50 mm to 400 mm, and most preferably 100 mm to 300 mm. The width D2 of the horn is preferably 10 mm to 40 mm, and most preferably 15 mm to 30 mm.

On the other hand, the elastic sheet F may be a thin film-like sheet having a thickness of 20 μm to 300 μm, preferably 30 μm to 200 μm, and most preferably 40 μm to 100 μm.

A thicker film will decrease the economical efficiency and the cutting property, and a thinner film will improve the wearability, but will have a decreased mechanical strength such that it may rip during the ultrasonic attachment.

As described above, as the edge portions 21a and 21c and the flat portion 21b of the protrusion 21 contact the vibrating horn 10 shown in FIGS. 4A to 4C, the non-woven fabrics W1 and W2 and the elastic sheet F are ultrasonically welded together at each attachment position M while forming the vent holes H1 and H2 in portions of the outer edge Mc of the attachment position M.

Therefore, since an adhesive made of a hotmelt resin, or the like, can be reduced significantly, it is possible to reduce the production cost. As the adhesive is reduced, it is also possible to prevent deterioration of the feel of the laminated stretchable sheet. Moreover, since it is not necessary to separately provide a step of forming vent holes, the process is easy, and the productivity will not be lowered.

INDUSTRIAL APPLICABILITY

The present invention can be employed as a method for producing a disposable worn article, for example.

The invention claimed is:

1. A method for producing a disposable worn article including a torso portion covering a torso of a wearer, and a crotch portion covering a crotch of the wearer, the method comprising:
    a step of forming stretched elastic sheet pieces from a continuous elastic sheet;
    a step of carrying a continuous web to be the torso portion in a longitudinal direction of the continuous web;
    a step of placing the elastic sheet pieces intermittently on the continuous web, with a stretch direction of the stretched elastic sheet pieces being aligned with the longitudinal direction;
    a step of bonding at least a part of opposite end portions of each of the elastic sheet pieces in the longitudinal direction to the continuous web by an adhesive without bonding an intermediate portion between the opposite end portions to the continuous web, during the placing step;
    an ultrasonic attachment step of applying a vibration energy on an overlap portion in which the intermediate portion of one of the elastic sheet pieces between the opposite end portions and the continuous web overlap with each other, thereby welding the intermediate portion to the continuous web, and forming a laminated stretchable sheet;
    a placement step of placing core portions, each of which forms the crotch portion, between adjacent one of the elastic sheet pieces on the laminated stretchable sheet; and
    a step of cutting off the laminated stretchable sheet between adjacent ones of the core portions and at the intermediate portion welded to the continuous web.

2. A method for producing a disposable worn article according to claim 1, further comprising:

a step of stretching the elastic sheet in a longitudinal direction;

a step of carrying a non-woven fabric, which forms a portion of the torso portion and which is to be an inner sheet to be in contact with a skin surface of the wearer;

a step of laying the elastic sheet in a stretched state on the non-woven fabric;

a step of bonding by an adhesive a portion of an overlap portion between the non-woven fabric and the elastic sheet laid on each other; and a step of cutting off the non-woven fabric and the elastic sheet, which have been bonded together, to thereby obtain a cut-off panel including one of the elastic sheet pieces therein, wherein the step of forming the elastic sheet piece is performed by these steps.

3. A method for producing a disposable worn article according to claim 2, wherein bonding portions in which the non-woven fabric and the elastic sheet are bonded together are formed in the opposite end portions of the elastic sheet piece in the stretch direction; and the placement step is performed so that the core portion covers at least a portion of the bonding portions.

4. A method for producing a disposable worn article according to claim 1, wherein the torso portion includes a front torso portion covering an abdominal portion of the wearer, and a rear torso portion covering a back portion of the wearer; and each of the elastic sheet pieces is placed on each of the torso portions, with the core portion placed so as to bridge between the front torso portion and the rear torso portion.

5. A method for producing a disposable worn article according to claim 4, wherein the front torso portion and the rear torso portion are a pair of continuous webs placed apart from each other, and the method comprises a step of carrying the pair of continuous webs in parallel to each other.

6. A method for producing a disposable worn article according to claim 4, further comprising, after the step of placing the elastic sheet pieces, a step of slitting the laminated stretchable sheet into a plurality of pieces along a carrying direction of the laminated stretchable sheet.

7. A method for producing a disposable worn article according to claim 1, further comprising:

a step of sandwiching the elastic sheet pieces between the continuous web and another web different from the continuous web thereby to form a composite sheet, wherein the two webs are non-woven fabrics containing thermoplastic fibers therein, and the elastic sheet is a thermoplastic resin sheet, wherein the ultrasonic attachment step is performed by applying a vibration energy, at a plurality of attachment positions, on an overlap portion between the two non-woven fabrics and the elastic sheet piece, thereby welding together the two non-woven fabrics and the elastic sheet piece; and in the ultrasonic attachment step, vent holes are formed in the elastic sheet piece, only in a portion of an outer edge of the attachment positions.

8. A method for producing a disposable worn article according to claim 7, wherein, in the ultrasonic attachment step, the plurality of attachment positions are dotted over the overlap portion, and the laminated stretchable sheet is formed by applying the vibration energy, at the dotted attachment positions, on the overlap portion of the composite sheet, thereby welding together the two non-woven fabrics and the intermediate portion of each of the elastic sheet pieces at the dotted attachment positions.

9. A method for producing a disposable worn article according to claim 8, wherein the ultrasonic attachment is performed between an anvil having a plurality of protrusions corresponding to the attachment positions and a horn for applying the vibration energy on the overlap portion of the composite sheet in cooperation with the anvil;

each of the protrusions being capable of facing the horn, and comprising a flat portion that is flat and an edge portion formed in a peripheral edge of the flat portion;

the protrusions being formed as the anvil along a periphery of a drum that rotates about a predetermined axis of the drum, the composite sheet is carried along with the rotation of the drum; and in the ultrasonic attachment, each of the protrusions intermittently contacts several times with the horn with various angles via the composite sheet, thereby welding together the two non-woven fabrics and the intermediate portion of each of the elastic piece portions between the protrusions and the horn, and forming vent holes on each of the stretched elastic sheet pieces by the edge portions of the protrusions at end portions of peripheral edges of the attachment positions in the carrying direction.

10. A method for producing a disposable worn article according to claim 3, wherein in the step of bonding by an adhesive the portion of the overlap portion between the non-woven fabric and the elastic sheet laid on each other, the non-woven fabric and at least a part to be one of the opposite end portions of each of the elastic sheet pieces are bonded to each other without bonding another part to be the intermediate portion of each of the elastic sheet pieces to the non-woven fabric.

* * * * *